(12) United States Patent
Galeotti et al.

(10) Patent No.: US 7,393,986 B2
(45) Date of Patent: Jul. 1, 2008

(54) PROCESS FOR THE PRODUCTION AND PURIFICATION OF VINYL AROMATIC MONOMERS

(75) Inventors: Armando Galeotti, Gonzaga-Mantova (IT); Elena Bencini, Virgilio-Mantova (IT); Leonardo Trentini, Mantova (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/583,376

(22) PCT Filed: Dec. 13, 2004

(86) PCT No.: PCT/EP2004/014166

§ 371 (c)(1),
(2), (4) Date: Dec. 28, 2006

(87) PCT Pub. No.: WO2005/063659

PCT Pub. Date: Jul. 14, 2005

(65) Prior Publication Data

US 2007/0142687 A1    Jun. 21, 2007

(30) Foreign Application Priority Data

Dec. 22, 2003  (IT) .......................... MI2003A2551

(51) Int. Cl.
*C07C 2/64* (2006.01)
*C07C 5/327* (2006.01)
*C07C 7/05* (2006.01)

(52) U.S. Cl. ............................ 585/323; 585/441; 203/9

(58) Field of Classification Search ................. 585/323, 585/441; 203/9
See application file for complete search history.

(56) References Cited

U.S. PATENT DOCUMENTS 3,408,265 A    10/1968    Ward

FOREIGN PATENT DOCUMENTS

DE            29 14 226       10/1980

*Primary Examiner*—Thuan Dinh Dang
(74) *Attorney, Agent, or Firm*—Oblon, Spivak, McClelland, Maier & Neustadt, P.C.

(57) ABSTRACT

Process for the production of vinyl aromatic monomers which comprises: a) feeding an aromatic stream and an olefinic stream to an alkylation unit; b) feeding the reaction product coming from the alkylation section to a first separation section; c) recovering the mono-alkylated aromatic hydrocarbon and the heavy bottom product from the first separation section; d) feeding the mono-alkylated aromatic to a dehydrogenation section; e) feeding the reaction product coming from the dehydrogenation section to a second purification/separation section; f) also feeding the heavy bottom product of step (c) to the second purification/separation section; g) recovering a stream consisting of the vinyl aromatic monomer with a purity higher than 99.7 by weight.

19 Claims, 1 Drawing Sheet

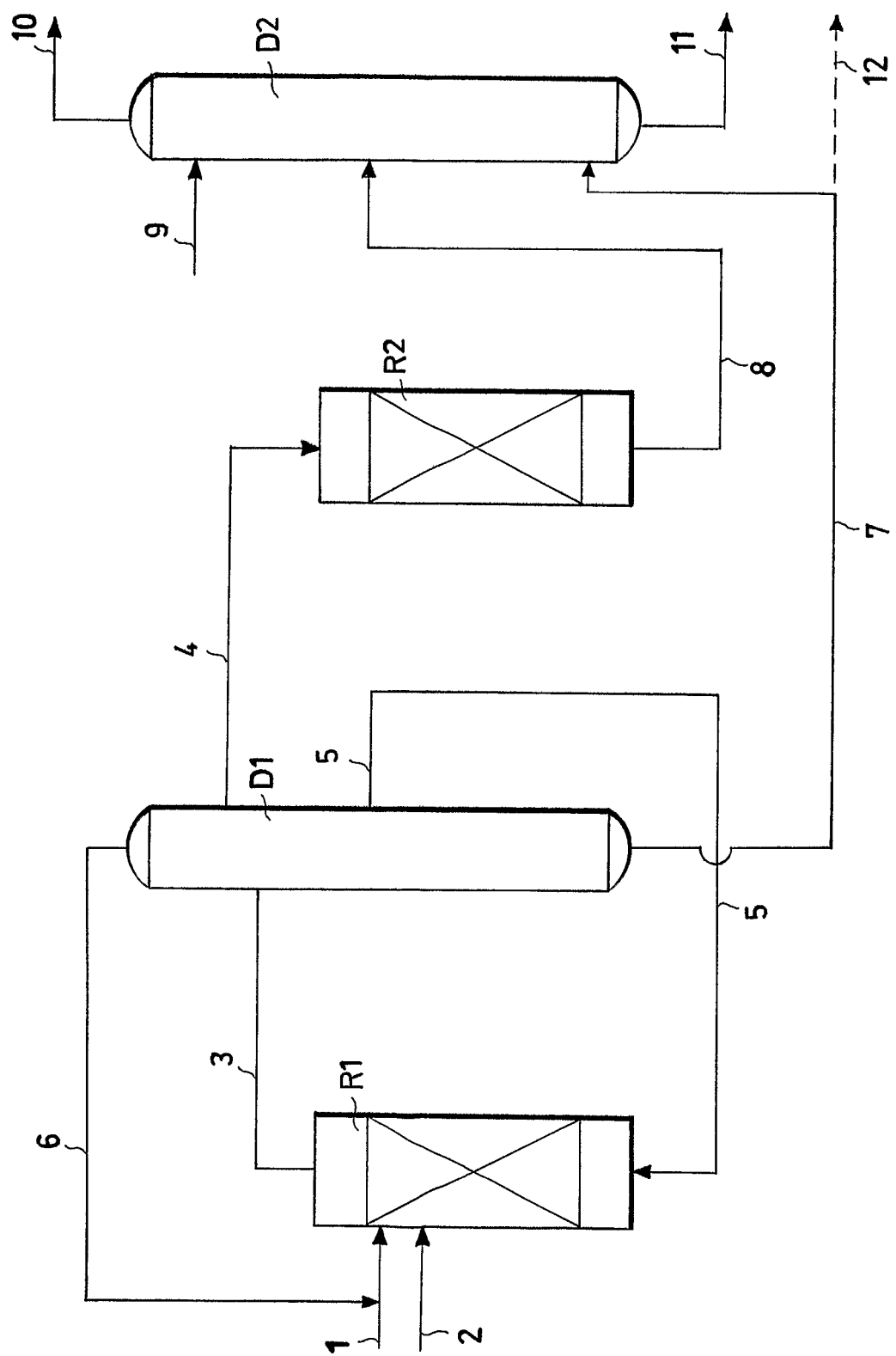

PROCESS FOR THE PRODUCTION AND PURIFICATION OF VINYL AROMATIC MONOMERS

The present invention relates to an improved process for the production and purification of vinyl aromatic monomers.

More specifically, the present invention relates to an improved process for the production and purification of vinyl aromatic monomers coming from the dehydrogenation of the corresponding alkylated products.

Even more specifically, the present invention relates to an improved process for the production and purification of styrene coming from the dehydrogenation of ethyl benzene.

Vinyl aromatic monomers, such as styrene, are particularly known for their use in the preparation of plastic materials, such as compact/crystalline polystyrene or expanded polystyrene. These monomers are recovered from the liquid effluents coming from a dehydrogenation section by means of a series of fractionation columns operating in series, with respect to the flow of vinyl aromatic monomer.

In the case of styrene, there are generally three or four fractionation columns depending on the type of process. The liquid mixture of aromatic hydrocarbons coming from the dehydrogenation section is fed into the first column. In this column, a mixture of benzene and toluene is separated at the head, which forms a by-product of the production process of styrene, whereas a stream containing non-reacted ethyl benzene, styrene and high-boiling products is extracted from the bottom. The stream coming from the bottom of the first column is fed to a second column, where a stream containing non-reacted ethyl benzene is separated at the head and recycled to the dehydrogenation section, whereas a stream containing styrene together with high-boiling products is extracted from the bottom. The flow coming from the bottom of the second column is fed to a third column, where the styrene forming the end-product is removed at the head, whereas a stream consisting of styrene and high-boiling products is extracted from the bottom. As the concentration of styrene present in the stream leaving the bottom of the third purification column is still high, it is further treated in a fourth column, where said stream is fed, or else to a different apparatus, such as an evaporator. A stream rich in high-boiling products which forms the process residue (waste stream) is produced and removed from the latter part of the purification section, whether it be a distillation column or an evaporator.

What is indicated above is one of the possible purification schemes of styrene. There is also a second scheme, based on three columns which is described hereafter. In this case the liquid hydrocarbon mixture is fed to the first column, where a mixture of benzene, toluene and ethyl benzene is separated at the top, whereas a stream containing styrene and high-boiling products is separated at the bottom. The product extracted from the head is fed to a second column where a mixture of benzene and toluene, which forms a by-product of the production process of styrene, is extracted from the head, whereas a stream containing non-reacted ethyl benzene is obtained at the bottom and is sent to the dehydrogenation unit. The stream coming from the bottom of the first column is fed to the third column, where purified styrene is extracted from the head, whereas a stream whose composition is similar to that described in the previous scheme, is obtained at the bottom, which, as it is still rich in styrene, is further treated to recover this with procedures similar to those described above.

The residue (waste stream), produced with both schemes, contains significant quantities of heavy, viscous materials consisting of pitches and/or other polymeric products which are formed as a result of the processing process. Vinyl aromatic monomers, for example styrene, tend to polymerize if they are subjected to the action of heat and consequently, during distillation, they tend to form solid polymeric residues which can be deposited and block the equipment associated with the purification system. In order to avoid or reduce this phenomenon, the purification of styrene requires the use of polymerization retardants or inhibitors such as, for example, stable nitroxide radicals used alone or combined with polymerization retardants such as, for example, aromatic nitro-derivatives, as described in U.S. Pat. Nos. 4,670,131, 5,254,760 and 5,910,232.

The Applicant has now found a new additive for preventing the premature polymerization of vinyl aromatic monomers, coming from the dehydrogenation of the corresponding alkylated products, particularly during the purification phase which, in the case of the use of nitroxide alone, strengthens its effect. Alternatively, this additive can substitute the retarding compound, when this is used in a combination with the nitroxide.

This new additive comes from the alkylation section which precedes dehydrogenation and consists of heavy products, essentially polyalkyl benzenes, which are formed during the alkylation reaction and which are separated in a specific purification section. It has, in fact, been surprisingly found that the heavier stream coming from the bottom of the distillation section, downstream of the alkylation reactor, if fed to the purification section of the vinyl aromatic monomer, inhibits its premature polymerization. This result is not only unexpected but is also useful as it allows a greater recovery of the monomer from the styrene distillation residues.

An object of the present invention therefore relates to an improved process for the production and purification of vinyl aromatic monomers which comprises:

a) feeding a stream consisting of an aromatic hydrocarbon together with a stream essentially consisting of a $C_2$-$C_3$ olefin, to an alkylation section;
b) feeding the reaction product coming from the alkylation section to a first separation section;
c) discharging from the first separation section, a first stream consisting of non-reacted aromatic hydrocarbon which is recycled to the alkylation section, a second stream essentially consisting of a mono-alkylated aromatic hydrocarbon, a third stream essentially consisting of dialkylated aromatic hydrocarbons, sent to a transalkylation section, and a fourth stream essentially consisting of a mixture of polyalkylated aromatic hydrocarbons;
d) feeding the second stream of step (c) to a dehydrogenation section;
e) feeding the reaction product coming from the dehydrogenation section to a second purification/separation section, comprising at least one distillation column;
f) feeding the fourth stream of step (c) to said at least one distillation column;
g) discharging from the head of said at least one distillation column, a stream consisting of the vinyl aromatic monomer having a purity higher than 99.7% by weight.

According to the present invention, the aromatic hydrocarbon fed to the alkylation section can be selected from those having from 6 to 9 carbon atoms but it preferably consists of benzene. Another aromatic hydrocarbon which can be used in the process object of the present invention is, for example, toluene.

The preferred aromatic hydrocarbon is benzene refinery grade with a purity higher than or equal to 95% by weight.

The $C_2$-$C_3$ olefinic stream, for example ethylene or propylene, also refinery grade with a purity higher than or equal to 95% by weight, is fed to the alkylation reactor together with the aromatic hydrocarbon, fresh and, optionally, recycled. The two aromatic and olefinic streams are fed to the alkylation unit so as to have aromatic/olefin molar ratios which satisfy the requirements of current technologies, generally from 2 to 50, preferably from 3 to 10.

The alkylation reaction is carried out with conventional catalytic systems, for example it can be carried out according to the method described in European patent 432,814.

Any alkylation reactor can be used in the process object of the present invention. For example fixed bed or fluid bed reactors, carrier reactors, reactors operating with a slurry mixture and catalytic distillation reactors, can be used.

The preferred alkylation catalysts can be aluminum trichloride or those selected from synthetic and natural porous crystalline solids based on silicon and aluminum, such as acid zeolites in which the silicon/aluminum atomic ratio ranges from 5/1 to 200/1. In particular, Y, beta, omega zeolites, mordenite and the crystalline porous solids MCM-22, MCM-36, MCM-49, are preferred. Alternatively, it is possible to use synthetic zeolites of the ZSM group in which the silicon/aluminum atomic ratio ranges from 20/1 to 200/1 such as ZSM-5 zeolite.

The alkylation reaction can be carried out under temperature and pressure conditions which depend not only on the catalyst selected but also on the type of reactor and choice of reagents. In the case of the alkylation of benzene with ethylene, the reaction temperature generally ranges from 50 to 450° C. More specifically, with zeolitic catalysts, for either fixed or mobile bed processes in gas phase, the temperature preferably ranges from 300 to 450° C. or from 180 to 250° C. for processes in liquid phase, whereas in the case of a catalytic distillation reactor, operating in mixed gas-liquid phase, the reaction temperature, varying along the catalytic bed, ranges from 140 to 350° C., preferably from 200 to 300° C. When reactors operating with a slurry mixture and an aluminum trichloride catalyst, are used, the temperature ranges from 100 to 200° C.

The pressure inside the alkylation reactor is maintained at values ranging from 0.3 to 6 MPa, preferably from 0.4 to 5 MPa.

The aromatic stream leaving the alkylation reactor is treated with conventional means for recovering the reaction product from the non-converted reagents and reaction byproducts. In particular, the separation system preferably consists of a series of at least three distillation columns from which the non-reacted aromatic compound is recovered from the first, and recycled to the alkylation reactor and/or a transalkylation unit described below. The mono-alkyl substituted aromatic compound, for example ethyl benzene, is recovered from the second distillation column and fed to the dehydrogenation unit, whereas the dialkylated aromatic products are recovered from the head of the third column and sent to the transalkylation unit, whereas the heavy products, essentially consisting of polyalkylated products, tetralines and alkyl substituted diphenyl ethanes, which form the polymerization inhibitor additive, are recovered from the bottom and fed to the purification/separation section of the vinyl aromatic compound.

The dialkylated aromatic compounds, for example diethyl benzenes, can be fed to a transalkylation reactor for transalkylation with $C_6$-$C_9$ aromatic hydrocarbons, for example benzene, to produce the corresponding mono-alkyl substituted aromatic compounds, such as ethyl benzene, and increase the yield of the alkylation production.

The transalkylation can take place in a specific reactor or in the same alkylation reactor.

The transalkylation reactor, when present, preferably consists of a reactor operating in slurry phase, when the catalyst is aluminum trichloride, or in a fixed bed reactor, functioning in liquid phase, in which a conventional zeolitic transalkylation catalyst is present, such as Y zeolite, beta zeolite or mordenite, preferably Y or beta zeolite. The transalkylation reaction can be carried out according to what is described in European patent 847,802.

In the case of the transalkylation of diethyl benzene with benzene, the benzene/ethylene molar ratio, calculated with respect to the total moles of benzene present as such and as diethyl benzene and the total moles of ethylene present as substituents in the diethyl benzenes, ranges from 2/1 to 18/1, preferably from 2.5/1 to 10/1. The temperature in the reactor is maintained at a value of 50 to 350° C., preferably from 130 to 290° C., whereas the pressure is maintained at 0.02 to 6 MPa, preferably from 0.4 to 5 MPa.

The mono-alkylated aromatic product is fed to the catalytic dehydrogenation section which comprises one or more reactors operating with a fixed bed or fluid bed, preferably with a fixed bed.

The dehydrogenation reaction with a fixed bed reactor takes place at a temperature ranging from 500 to 700° C., preferably from 550 to 650° C., at a pressure ranging from 0.02 to 0.15 MPa, in the presence of a catalyst based on iron oxide and potassium carbonate containing other metallic compounds in small quantities having the function of promoters.

In the case of the production process of styrene, the dehydrogenation can take place, for example, with a fixed bed catalyst by feeding a mixture of ethyl benzene vapour and water vapour, in a water/ethyl benzene molar ratio ranging from 5 to 15, preferably from 6 to 12, onto a first reactor in which a partial conversion of ethyl benzene takes place. The reacted mixture leaving the first reactor is fed to a second reactor, after the temperature has been brought to the required value by means of a heat exchanger. The reaction mixture, in which the ethyl benzene is converted for at least 60%, is cooled and condensed before being sent to the purification section. If required, at the outlet of the second reactor, it is possible to include a third reactor to increase the conversion of ethyl benzene up to and over 70%.

The reaction product leaving the dehydrogenation phase is fed to a second purification/separation section for the recovery of the vinyl aromatic monomer, for example styrene. The purification section comprises at least one distillation column even if it is preferable to operate with three or four distillation columns connected in series with respect to the flow of the monomer to be purified.

The heavy bottom product coming from the separation section of the alkylated product is also fed to the second purification/separation section in order to prevent the premature polymerization of the vinyl aromatic monomer and limit the consumption of polymerization inhibitor and/or retardant additives which are necessarily and conventionally used in this section. The feeding can be effected in any of the distillation columns, at any height thereof and, optionally, by premixing said heavy bottom product with any of the streams present in said second purification/separation section.

In particular, the columns of the second purification/separation section can be selected from those which contain conventional trays or random and/or structured packing. In order to keep the internal temperatures as low as possible to prevent the thermal polymerization of the vinyl aromatic monomer, the columns operate at a low pressure, generally ranging from 0.002 to 0.03 MPa.

In addition to the liquid mixture coming from the dehydrogenation section, a small flow is also fed to the single columns, containing a substance which acts as polymerization inhibitor, for example (in the case of the purification and separation of styrene) 4-hydroxy-2,2,6,6-tetramethyl-piperidin-1-oxy, 2,2,6,6-tetra-methyl-piperidin-1-oxy, or any of the products described in U.S. Pat. No. 4,670,131, and in some cases also a further flow which contains a substance which acts as polymerization retardant, for example sulfur, t-butyl catechol or dinitro-phenols and phenylene diamines described in U.S. Pat. No. 4,466,905. This means of operating limits the loss of vinyl aromatic monomer due to its polymerization which transforms it into a high-boiling product, subsequently eliminated as residue.

The bottom product recovered at the bottom of the third or fourth distillation column consists of a stream rich in high-boiling products, of which a considerable quantity consists of vinyl aromatic polymer formed in the purification section itself as a result of the distillation process and can still contain a significant quantity of monomer. This stream is a waste product of the process which is generally sent for thermo-destruction.

From what is specified above, it is therefore evident that one of the most important objectives of the purification process of vinyl aromatic monomers is to adopt solutions useful for minimizing the formation of polymer as much as possible, to improve the efficiency of the process by limiting the formation of waste product, and to avoid fouling phenomena associated therewith which can cause operating problems and the necessity for expensive maintenance.

The bottom stream leaving the separation section of the alkylated products, consisting of a mixture of polyalkylated aromatic hydrocarbons together with other heavy impurities, is fed to one of the distillation columns, preferably the first column. This stream not only acts as a diluent of the distillation column residues allowing a greater recovery of the monomer but also, surprisingly, as a polymerization retardant, contributing to reduce the overall quantity of waste product of the entire process as well as allowing a reduction in the consumption of the substances which inhibit or retard polymerization. As this stream essentially consists of high-boiling compounds, it flows through the residues of the distillation column of the second purification/separation section and is extracted from the bottom of the last column together with the residues associated with the dehydrogenation. For the above reasons, the stream deriving from the bottom of said column in the process scheme object of the present invention, to be sent for thermo-destruction, is significantly reduced with respect to the sum of the two corresponding separated streams deriving respectively from the purification section of the alkyl aromatic product and the vinyl aromatic monomer in the traditional processes of the known art.

An example is provided below which demonstrates the inhibiting effect, on the polymerization of styrene, of the bottom product coming from the purification unit of the synthesis section of ethyl benzene and an applicative example which uses a scheme illustrated in the enclosed FIGURE.

EXAMPLE 1

A first solution of inhibitor 4-HT (1-oxy-2,2,6,6-tetramethyl piperidin-4-ol) in styrene at a concentration of 5 ppm (test A) and a second solution in styrene of the same inhibitor at 5 ppm and 1.5% of polyethyl benzenes (PEB) coming from the bottom of the purification unit of a plant for the production of ethyl benzene (test B), are prepared in a feeding vessel. In both tests A and B, the solution containing the inhibitor is fed for about 18 hours in continuous, into a mechanically stirred jacketed reactor and maintained at a temperature of 95° C. The product leaves the reactor by means of a valve situated on the bottom. The feeding and discharge flow-rate are regulated so as to have a constant residence time inside the reactor equal to an hour.

Before each test, the system is treated by nitrogen bubbling in order to eliminate the oxygen and the apparatus is maintained under a nitrogen seal for the whole duration of the test. At the end of 18 hours a sample of effluent corresponding to the stationary state of the system (so-called "zero time") is removed and the polymer content is determined (weight %).

This determination is effected by turbidimetry if the concentration of the polymer is lower than 1000 ppm or by precipitation with ethanol for higher quantities.

The feeding is then interrupted and the valve situated on the bottom of the reactor is contemporaneously intercepted, thus closing the system on itself (so-called shut off). Samples are taken from the reactor at pre-established times for an overall duration of the test of 7 hours, following the formation kinetics of the polymer in the presence of the residual inhibitor at that given temperature.

The following table indicates the results of the most significant tests (polymer content in weight %), effected at a temperature of 95° C., which unequivocally show the retarding effect of the PEB.

TABLE 1

| Shut off time (min) | Polystyrene % (4-HT) Test A | Polystyrene % (4-HT + PEB) Test B |
|---|---|---|
| 0 | 0 | 0 |
| 60 | 1.7 | 0.11 |
| 120 | 2.9 | 0.39 |
| 180 | 4.5 | 0.60 |
| 240 | 6.5 | 0.93 |
| 360 | 9.8 | 1.95 |
| 420 | 11.6 | 2.36 |

EXAMPLE 2

Reference is made to the enclosed FIGURE which represents a simplified scheme of a process on an industrial scale for the production and purification of styrene, and in which the main operating steps are exclusively indicated.

In the scheme R1 represents the alkylation reactor, R2 is the dehydrogenation reactor, D1 is the first separation section to recover the alkylated aromatic hydrocarbon whereas D2 represents the second purification/separation section of the dehydrogenated product.

The numbered streams and respective weight flow-rates are illustrated and explained in Table 2 below.

| R1 = alkylation/transalkylation reactor | |
|---|---|
| Temperature | 170° C. |
| Pressure | 4.6 barA |
| Benzene/ethylene weight ratio | 7.4 |
| R2 = dehydrogenation reactor | |
| Temperature | 600° C. |
| Pressure | 0.5 barA |

TABLE 2

| | | |
|---|---|---|
| (1) = Fresh benzene | kg/h | 19,000 |
| (2) = ethylene | kg/h | 5,700 |
| (3) = alkylated product | kg/h | 54,700 |
| (6) = recycled benzene | kg/h | 23,000 |
| (4) = ethyl benzene for dehydrogenation | kg/h | 32,000 |
| (5) = recycled diethyl benzene | kg/h | 7,000 |
| (7) = PEB fed to D2 | kg/h | 300 |
| (12) = PEB fed to the torch | kg/h | 300 |
| (8) = Dehydrogenated product | kg/h | 32,000 |
| (9) = TEMPO | kg/h | 3.6 |
| (10) = Styrene in the case of (7) | kg/h | 20,070 |
| (10) = Styrene in the case of (12) | kg/h | 20,000 |
| (11) = heavy products in the case of (7) | kg/h | 460 |
| (11) = heavy products in the case of (12) | kg/h | 230 |

TEMPO = 1-oxy-2,2,6,6-tetramethyl piperidin-4-ol

The invention claimed is:

1. An improved process for the production and purification of vinyl aromatic monomers which comprises:
   a) feeding a stream consisting of an aromatic hydrocarbon together with a stream essentially consisting of a $C_2$-$C_3$ olefin, to an alkylation section;
   b) alkylating the aromatic hydrocarbon by reaction with the $C_2$-$C_3$ olefin in the alkylation section;
   c) feeding the alkylation reaction product coming from the alkylation section to a first separation section;
   e) discharging from the first separation section:
      a first stream consisting of non-reacted aromatic hydrocarbon which is recycled to the alkylation section,
      a second stream consisting essentially of a mono-alkylated aromatic hydrocarbon,
      a third stream consisting essentially of dialkylated aromatic hydrocarbons, sent to a transalkylation section, and
      a fourth stream consisting essentially of a mixture of polyalkylated aromatic hydrocarbons;
   e) feeding the second stream of step (d), consisting essentially of mono-alkylated aromatic hydrocarbon to a dehydrogenation section;
   f) dehydrogenating the mono-alkylated aromatic hydrocarbon to form a vinyl aromatic monomer;
   g) feeding a reaction product coming from the dehydrogenation section to a second purification/separation section, comprising at least one distillation column;
   h) feeding the fourth stream of step (d) consisting essentially of a mixture of polyalkylated aromatic hydrocarbons to said at least one distillation column of step g);
   i) discharging from a head of said at least one distillation column of step (g), a stream consisting of the vinyl aromatic monomer having a purity higher than 99.7% by weight.

2. The process according to claim 1, wherein the aromatic hydrocarbon fed to the alkylation section is refinery grade benzene, and the $C_2$-$C_3$ olefin is refinery grade ethylene or propylene.

3. The process according to claim 2, wherein the $C_2$-$C_3$ olefin is refinery grade ethylene.

4. The process according to claim 1, wherein a molar ratio of aromatic hydrocarbon to $C_2$-$C_3$ olefin is from 2 to 50.

5. The process according to claim 1, wherein the alkylation reaction takes place in the presence of catalysts selected from the group consisting of aluminum trichloride, synthetic and natural porous crystalline solids based on silicon and aluminum in which the silicon/aluminum atomic ratio ranges from 5/1 to 200/1 and synthetic zeolites of the ZSM group in which the silicon/aluminum atomic ratio ranges from 20/1 to 200/1.

6. The process according to claim 1, wherein the alkylation reaction is carried out at a temperature ranging from 50 to 450° C.

7. The process according to claim 3, wherein the alkylating is catalyzed by aluminum trichloride and the temperature ranges from 100 to 200° C.

8. The process according to claim 1, wherein the alkylation reaction is carried out at a pressure ranging from 0.3 to 6 MPa.

9. The process according to claim 1, wherein the aromatic stream leaving the alkylation reactor is fed to a separation system consisting of a series of at least three distillation columns for the recovery of at least the mono-alkyl substituted aromatic compound, to be sent to the dehydrogenation unit, and a heavy bottom product consisting essentially of polyalkylated products, tetralines and alkyl substituted diphenyl ethanes.

10. The process according to claim 1, wherein the dehydrogenation reaction takes place in a fixed bed reactor, at a temperature ranging from 500 to 700° C., at a pressure ranging from 0.02 to 0.15 MPa, in the presence of a catalyst based on iron oxide and potassium carbonate.

11. The process according to claim 1, wherein the second purification/separation section comprises three or four distillation columns connected in series with respect to a flow of vinyl aromatic monomer to be purified.

12. The process according to claim 1, wherein the fourth stream consisting essentially of a mixture of polyalkylated aromatic hydrocarbons leaving the separation section of alkylated products is sent to any of the distillation columns, at any height thereof and, optionally, by premixing said heavy bottom product with any of the streams present in said second purification/separation section.

13. The process according to claim 12, wherein the fourth stream consisting essentially of a mixture of polyalkylated aromatic hydrocarbons leaving the separation section of alkylated products is sent to the first distillation column of the second purification/separation section.

14. The process according to claim 3, wherein a molar ratio of refinery grade benzene to refinery grade ethylene is from 2 to 50.

15. The process according to claim 3, wherein the alkylation reaction takes place in the presence of catalysts selected from the group consisting of aluminum trichloride, synthetic and natural porous crystalline solids based on silicon and aluminum in which the silicon/aluminum atomic ratio ranges from 5/1 to 200/1 and synthetic zeolites of the ZSM group in which the silicon/aluminum atomic ratio ranges from 20/1 to 200/1.

16. The process according to claim 3, wherein the alkylation reaction is carried out at a temperature ranging from 50 to 450° C.

17. The process according to claim 3, wherein the dehydrogenation reaction takes place in a fixed bed reactor, at a temperature ranging from 500 to 700° C., at a pressure ranging from 0.02 to 0.15 MPa, in the presence of a catalyst based on iron oxide and potassium carbonate.

18. The process according to claim 3, wherein the fourth stream consisting essentially of a mixture of polyalkylated aromatic hydrocarbons leaving the separation section of alkylated products is sent to any of the distillation columns, at any height thereof and, optionally, by premixing said heavy bottom product with any of the streams present in said second purification/separation section.

19. The process according to claim 18, wherein the fourth stream consisting essentially of a mixture of polyalkylated aromatic hydrocarbons leaving the separation section of alkylated products is sent to the first distillation column of the second purification/separation section.

* * * * *